United States Patent
Muguerza Marquínez et al.

(10) Patent No.: US 8,946,383 B2
(45) Date of Patent: Feb. 3, 2015

(54) OBTAINING COCOA EXTRACTS RICH IN BIOACTIVE PEPTIDES WITH ACE AND PEP ENZYME INHIBITORY ACTIVITY

(75) Inventors: Begoña Muguerza Marquínez, Valencia (ES); Honorato Monzo Oltra, Paterna (ES); Natalia Alepuz Rico, Valencia (ES); Esther Bataller Leiva, Valencia (ES); Salvador Genoves Martínez, Valencia (ES); Maria Enrique López, Castellon (ES); Patricia Guerola Guerola, Valencia (ES); Daniel Ramon Vidal, Valencia (ES)

(73) Assignee: Naturex, Avignon (FR)

( * ) Notice: Subject to any disclaimer, the term of this patent is extended or adjusted under 35 U.S.C. 154(b) by 521 days.

(21) Appl. No.: 13/056,909

(22) PCT Filed: Aug. 1, 2008

(86) PCT No.: PCT/ES2008/000540
§ 371 (c)(1),
(2), (4) Date: Apr. 27, 2011

(87) PCT Pub. No.: WO2010/012845
PCT Pub. Date: Feb. 4, 2010

(65) Prior Publication Data
US 2011/0213122 A1  Sep. 1, 2011

(51) Int. Cl.
A61K 38/10    (2006.01)
C07K 7/08     (2006.01)
A23G 1/00     (2006.01)
A23G 1/30     (2006.01)
A23L 1/30     (2006.01)
A23L 1/305    (2006.01)

(52) U.S. Cl.
CPC ........... *A23G 1/0006* (2013.01); *A23G 1/0009* (2013.01); *A23G 1/30* (2013.01); *A23L 1/3002* (2013.01); *A23L 1/3053* (2013.01); *C12Y 304/15001* (2013.01); *A23V 2002/00* (2013.01)
USPC ........................................ 530/327; 514/21.5

(58) Field of Classification Search
None
See application file for complete search history.

(56) References Cited

U.S. PATENT DOCUMENTS

| 2008/0148432 A1* | 6/2008 | Abad ........................... 800/279 |
| 2011/0213122 A1* | 9/2011 | Muguerza Marquinez et al. ........................... 530/326 |
| 2013/0035291 A1* | 2/2013 | Bataller Leiva et al. ..... 514/15.7 |

FOREIGN PATENT DOCUMENTS

| ES | 2 264 394 A1 | 12/2006 |
| ES | 2 277 516 A1 | 7/2007 |
| JP | 2008-019228 A | 1/2008 |
| WO | 91/19800 A1 | 12/1991 |
| WO | WO 9119800 | * 12/1991 | ............. C12N 15/29 |
| WO | WO 0141775 | * 6/2001 | ............. A61K 35/00 |

OTHER PUBLICATIONS

Martorell et al., "A Cocoa Peptide Protects *Caenorhabditis elegans* from Oxidative Stress and β-Amyloid Peptide Toxicity", PLoS ONE 8(5):e63283 (doi:10.1371/journal.pone.0063283) (2013).

* cited by examiner

*Primary Examiner* — Maury Audet
(74) *Attorney, Agent, or Firm* — Sughrue Mion, PLLC

(57) ABSTRACT

The present invention relates to obtaining bioactive peptides from plant raw materials, specifically cocoa extracts, by means of enzyme treatment. Said biopeptides have angiotensin converting enzyme (ACE) and prolyl endopeptidase enzyme (PEP) inhibitory activity in vitro and/or antioxidant activity in vivo, being able to be used in the food, dietetic and pharmaceutical industry.

9 Claims, 5 Drawing Sheets

OBTAINING COCOA EXTRACTS RICH IN BIOACTIVE PEPTIDES WITH ACE AND PEP ENZYME INHIBITORY ACTIVITY

CROSS REFERENCE TO RELATED APPLICATIONS

This application is a National Stage of International Application No. PCT/ES2008/000540 filed Aug. 1, 2008, the contents of all of which are incorporated herein by reference in their entirety.

TECHNICAL FIELD OF THE INVENTION

The present invention relates to obtaining bioactive peptides from plant raw materials, specifically cocoa extracts, by means of enzyme treatment. Said biopeptides have angiotensin converting enzyme (ACE) and prolyl endopeptidase enzyme (PEP) inhibitory activity in vitro and/or antioxidant activity in vivo, being able to be used in the food, dietetic and pharmaceutical industry.

BACKGROUND OF THE INVENTION

The proteins present in foods are precursors of a large amount of peptides with some type of special biological activity, with useful properties on different processes of the organism. Due to the enormous interest in developing natural products which have some type of "extra" beneficial effect for the health of the person who consumes them, obtaining some of these biopeptides formed from different plant raw materials, it would be a good chance to develop new functional ingredients or products. The possibility of generating these peptides is a field of state of the art research in the nutraceutical industry because it allows generating new applications in functional foods, giving added value of food components and byproducts, improving the nutritive properties of conventional foods and developing new dietary supplements or even new medicinal products.

Some byproducts of the agro-food industry have a high content of proteins and bioactive peptides which provide added value to the same. There are different mechanisms for favoring the increase of peptides by considerably enriching a matrix and assigning it determined characteristics, such as for example, antihypertensive, antihyperglycemic, antineurodegenerative, anticariogenic, and even antihyperlipidemic characteristics. With the use of proteolytic enzymes, proteins can be hydrolyzed at specific points, capable of generating a broad spectrum of peptides in the hydrolyzed products obtained with multiple physiological effects.

The present invention is focused on obtaining cocoa extracts rich in peptides with ACE and PEP enzyme inhibitory activity.

The angiotensin converting enzyme (ACE) catalyzes the conversion of inactive angiotensin I into angiotensin II, which is a strong vasoconstrictor, so one of the current therapies used in the treatment of hypertension consists of the administration of drugs inhibiting this enzyme. In recent years, due to the side effects caused by drugs, natural inhibitors which would help in controlling hypertension in a less aggressive manner have been described. Among others, Takayanagi et al. ("Angiotensin I converting enzyme-inhibitory peptides from wine"; Am. J. Enol. Vitic, 50:65-68 1999) describe ACE inhibitory peptides from wine and Wu et al. ("Hypotensive and physiological effect of angiotensin converting enzyme inhibitory peptides derived from soy protein on spontaneously hypertensive rats"; J. Agric Food Chem, 49:501-506 2001) describe soy peptides which also have an inhibitory effect on ACE. Many other works, such as that of Pedroche et al. ("Utilisation of chickpea protein isolates for production of peptides with angiotensin I-converting enzyme (ACE)-inhibitory activity"; Journal of the Science of Food and Agriculture, 82:960-965 2002); Tomita et al. ("Potent Antibacterial Peptides Generated by Pepsin Digestion of Bovine Lactoferrin"; J Dairy Sci, 74:4137-4142 1991); Fujita et al. ("LKPNM: a_product-type ACE-inhibitory peptide derived from fish protein"; Immunopharmacology, 82:960-965 2002); Pihlanto-Leppalla et al. ("Angiotensine I-converting enzyme inhibitory properties of whey protein digests: concentration and characterization of active peptides"; J Dairy Research, 67:53-64 2000), and Yamamoto (Yamamoto., "Antihypertensive Peptides Derived from Food Proteins"; Biopolymers, 43(2): 129-134 1997), assert that peptides derived from different food matrices produce the inhibition of the angiotensin converting enzyme. Thus, document JP 6128287 relates to obtaining a peptide which inhibits the activity of the angiotensin and is obtained by hydrolysis of a milk protein; and JP 188282 describes twenty-three tripeptides which are useful as antihypertensive agents and are obtained by treating sardine muscles with proteases.

Document ES 2 253 036 B1 describes bioactive peptides derived from egg white proteins by means of enzymatic hydrolysis. Said peptides have angiotensin converting enzyme inhibitory activity (ACE-inhibitory activity) in vitro and/or antihypertensive activity in rats and/or antioxidant activity. The whole hydrolyzed products, the low molecular weight fractions thereof, and their constituent peptides could be used as therapeutic substances with ACE-inhibitory and/or antihypertensive and/or antioxidant activity.

Among the patent documents which mention peptides obtained from cocoa, WO 02/42327 A2 describes obtaining and purifying 2S albumin from cocoa beans. The enzymatic hydrolysis of proteins, which generates aroma, peptide and amino acid precursors which give rise to a cocoa aroma after heating with sugar.

Though some authors find ACE inhibitors in chocolate, this inhibition is generally associated with polyphenols, as is the case of Actis-Goretta et al. ("Inhibition of Angiotensin Converting Enzyme Activity by Flavonol-Rich Foods"; Agric. Food Chem, 54:229-234 2006) and of patent document WO 01/41775 A2, which describes the use of cocoa polyphenols, specifically procyanidins, in the modulation of inflammatory pathways, in the maintenance of vascular health in mammals and as antibacterial treatments. However, patent document JP 2008019228 describes an ACE inhibitor for food use and for treating hypertension comprising a composition of amino acids derived from cocoa extracts from which the polyphenols have previously been extracted. Said document does not specify the peptide/amino acid sequence nor does it give its size range, nor does it mention any type of enzymatic hydrolysis in the process of isolating and/or purifying the extracts having ACE inhibitory activity.

Prolyl endopeptidase (PEP) activity is related to memory loss and learning processes since it degrades neuropeptides rich in proline, such as vasopressin and the substance P involved in these processes. Some studies also indicate that this enzyme could be related to Alzheimer's disease. Until now, different authors, such as Kim et al. ("Prolyl Endopeptidase Inhibitors from Green Tea"; Arch Pharm Res, 24 (4): 292-296 2001) and Tezuka et al. ("Screening of crude drug extracts for prolyl endopeptidase inhibitory activity"; Phytomedicine, 6(3): 197-203 1999), assert that the polyphenols of certain plant extracts cause prolyl endopeptidase inhibition. Patent document US 2007/0116779 also describes the use of cocoa beans as a source of polyphenols, as one of the elements of pharmaceutical compositions, as an inhibitor of certain enzymes involved in neurodegenerative diseases, such as Alzheimer's or Parkinson's.

Other authors, such as Maruyama et al. ("Prolyl Endopeptidase Inhibitory Activity of Peptides in the Repeated Sequence of various Proline-Rich proteins"; Journal of Fermentation and Bioengineering, 74:145-148 1992) and Asano et al. ("Inhibition of prolyl endopeptidase by synthetic peptide fragments of human β-casein"; Agric. Biol. Chem, 55(3): 825-828 1991) argue that some peptide fragments inhibit the action of PEP, but until now no one has referred to cocoa peptides as inhibitory metabolites of said enzyme.

Therefore, due to the increasing greater demand for new ingredients and compounds with this type of inhibitory activity, given the healthy characteristics of cocoa, the possibility of finding bioactive peptides from their extracts having ACE activity has been considered, and several have surprisingly been found which not only have ACE inhibitory activity in vitro, but said bioactive peptides also have PEP inhibitory activity in vitro. Furthermore, they also show antioxidant activity in vivo according to tests with C. elegans.

OBJECT OF THE INVENTION

The present invention provides a method for obtaining cocoa extracts rich in bioactive peptides with ACE and PEP enzyme inhibitory activity in vitro and/or antihypertensive activity and/or activity antineurodegenerative and/or antioxidant activity in vivo, by means of the enzymatic hydrolysis of said extracts.

Specifically, the invention is based on obtaining cocoa extracts from cocoa containing ACE enzyme and PEP enzyme bioactive peptide inhibitors for the purpose of being able to be used as ingredients for their incorporation in functional foods. The bioactive peptides are produced by hydrolysis of one or more proteins or peptides present in the cocoa extracts obtained. For this purpose, enzymes and hydrolysis conditions which allow obtaining the desired biopeptides are used.

Different methodologies can be used to study these inhibitions. The in vitro assays are based on determining the enzyme activity of the ACE and PEP enzymes in the presence of the inhibitor to be assayed, i.e., the cocoa extracts rich in peptides in the present invention. Dilution tests were performed on the positive extracts for the purpose of determining the $IC_{50}$ (concentration of the hydrolyzed product necessary for inhibiting ACE and PEP enzyme activity by 50%) and obtaining quantitative data which can be used to compare the results.

The bioactive peptides or the hydrolyzed products containing them can be incorporated in functional foods. Once the extracts are concentrated, they can be used not only in the food industry and in dietetic products but also in the pharmaceutical industry by means of the manufacture of medicinal products with the suitable amount of said peptides, which medicinal products can be used in the treatment and prevention of diseases, such as the control of blood pressure, specifically hypertension, and also degenerative-type diseases, such as Alzheimer's, Parkinson's, etc. They can also be used as antioxidants.

The invention thus finds new applications of cocoa, contributing to its value increase from the health point of view.

A search for sequences of the bioactive peptides object of the present invention was conducted in different databases. The result gave no sequence identical to and with the same size as those described in the present invention.

The obtained results are several documents from the non-patent literature [a] Sousa Silva et al. "Phylogenetic analysis of Theobroma (Sterculiaceae) based on Kunitz-like trypsin inhibitor sequences", Plant Systemics and Evolution (2005), 250(1-2), 93-104; b) Kochhar et al. "Primary Structure of the Abundant Seed Albumin of Theobroma cacao by Mass Spectrometry", Journal of Agricultural and Food Chemistry (2000), 48(11), 5593-5599; c) "Cloning and sequencing of a gene encoding a 21 kDa trypsin inhibitor from Theobroma cacao L.", Cafe, cacao, The (1994), 38(2), 113-18; d) Tai et al. "Nucleic Acid Sequence of a 21 kDa cocoa seed protein with homology to the soybean trypsin inhibitor (Kunitz) family of protease inhibitors", Plant Molecular Biology (1991), 16(5), 913-15; and e) Spencer et al. "Cloning and sequencing of the cDNA encoding the major albumin of Theobroma cacao. Identification of the protein as a member of the Kunitz protease inhibitory family", Planta (1991), 183(4), 528-35], which relate to sequences that are part of the 21-23 kD precursors and of the trypsin inhibitor and which contain the amino acid sequences corresponding to the peptides sought. Furthermore, patent document WO 91/19800 A1 claims two proteins from cocoa beans which have a molecular weight of 21 kD or 23 kD, or a fragment thereof, comprising at least 6 amino acids, wherein after the protein or fragment is roasted, it forms at least one of the essential flavoring components of cocoa. Said document identifies the two 21 kD and 23 kD proteins, but it neither identifies nor mentions any peptide isolated therefrom.

Therefore, the present invention is considered a selection invention with respect to said document, i.e., it is novel because its components, in this case bioactive peptides, are not described individually, and therefore they are not part of the prior art per se. Furthermore, they present inventive step because they are the basis of a completely different invention and are not related to any other component which, once roasted, confers flavor to the cocoa object of the invention of the mentioned document. In fact, said invention is completely different from the use of the biopeptides of the present invention which are used in functional foods and in the pharmaceutical industry as controlling agents of hypertension, memory loss and neurodegenerative processes, because not only do they inhibit ACE enzyme activity but they also inhibit PEP enzyme activity in vitro, and the results in vivo initially indicate that they also have antioxidant capacity.

BRIEF DESCRIPTION OF THE INVENTION

This invention provides a method for obtaining cocoa extracts rich in peptides with antihypertensive and antineurodegenerative activity. The invention is specifically based on obtaining different extracts from a cocoa byproduct (bark) and the enzymatic hydrolysis thereof to obtain inhibitory bioactive peptides of the ACE enzyme and the PEP enzyme, for the purpose of being able to use them as ingredients for their incorporation in functional foods. According to the description of the present invention, the extracts obtained can be useful for their use not only in the food industry but also in the dietetic product industry and pharmaceutical industry.

In another aspect, the invention is related to the purification of the peptides of the cocoa extracts obtained. Depending on the peptides present in the extract, different purification strategies are performed, for example, concentration by cation exchange or hydrophobic interaction, and separation, for example by reverse-phase separation or gel filtration.

DETAILED DESCRIPTION OF THE INVENTION

Figure 1:
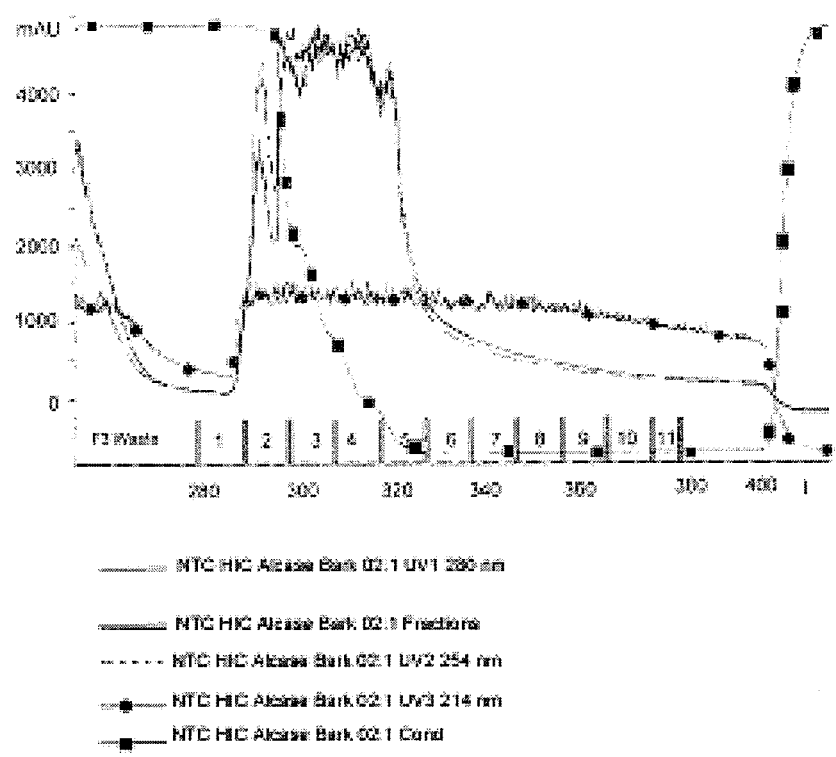
FIG. 1 shows a hydrophobic interaction chromatograph of the bark extract.

The present invention provides a method for obtaining bioactive peptides from cocoa extracts. Said bioactive peptides are those identified with the amino acid sequences referred to as: SEQ. ID. No. 1, SEQ. ID. No. 2, SEQ. ID. No. 3, SEQ. ID. No. 4, SEQ. ID. No. 5, SEQ. ID. No. 6, SEQ. ID. No. 7, and SEQ. ID. No. 8 (Table 4), which have ACE and PEP inhibitory activity in vitro and/or antioxidant activity in vivo. The invention further provides the use of said bioactive peptides as functional ingredients for different foods, considering as foods any composition intended for food, regardless of if it is in liquid or solid form.

The starting material of the present invention could be any suitable substrate which comprises one or more of the bioactive peptides of the Table 4. In a particular embodiment, said raw material is plant raw material, the starting material is specifically cocoa. Theobroma cacao is the scientific name of the cocoa tree. Cacao is Mayan (Ka'kaw) and Theobroma means food of the gods in Greek.

There are three main varieties of cocoa: criollo or native cocoa is the real cocoa and was named by the Spanish when they arrived in Mexico. It is cultivated in the Americas in Venezuela, Honduras, Colombia, Ecuador, Nicaragua, Guatemala, Trinidad, Jamaica, Mexico and Granada; and in the Caribbean, in the Indian Ocean area and in Indonesia. It is a cocoa recognized as having a very high quality, with little tannin content, and is reserved for manufacturing the finest chocolates. The forastero variety is originally from upper Amazonia. It is a normal cocoa, with the highest tannin levels. It is the most widely cultivated and is usually from Africa. The bean has a thick shell, is resistant and not very aromatic. To neutralize its imperfections, it requires intense roasting, where the flavor and burnt aroma of most chocolates comes from. Finally, the hybrids, especially trinitario, are a mix between the criollo and forastero. As its name suggests, it is originally from Trinidad where, after a terrible hurricane in 1727 destroyed virtually all the plantations on the island, it came about as a result of a cross-breeding process. The cocoa of the present invention can belong to any of the aforementioned varieties, including any of their hybrids.

In the present invention, the raw material is plant raw material and is a cocoa byproduct referred to as bark, which is cocoa with the husk partially defatted by means of physical pressing, with a fat proportion that can range between 5% and 15%, preferably 10%, expressed in weight percentage.

Said starting material is dissolved in water in a proportion that can range between 5% and 20%, preferably 10%. Once the bark has dissolved in the water, it is treated at different temperatures, for example between 40° C. and 60° C., preferably 50° C., for different times, for example between 1 hour and 24 hours, preferably 1, 6, 18 or 24 hours, with one or more hydrolytic enzymes at different concentrations. Any enzyme capable of providing the peptides of interest can be used. Specifically, the enzymes used could be both enzymes with cellulose activity, as is the case of the enzyme Termamyl, and enzymes with protease activity, such as the enzymes Alcalase, Neutrase, Ultraflo or Flavourzyme. A single enzyme or combinations of two or more enzymes can be used, provided that they produce one or more biopeptides with the desired characteristics. The enzyme concentrations used will range between 0.10 and 10 µl/L, and between 0.5 and 2 µl of enzyme per g of raw material. The hydrolysis conditions: pH, temperature, pressure, concentration of enzyme(s), time of the reaction, etc. are optimized depending on the enzyme or enzymes used.

To obtain the extract, once the hydrolysis reaction has ended, centrifugation at 4000 rpm for 15 minutes is performed and the supernatant containing the bioactive peptides object of the present invention is collected.

Another additional aspect of the invention relates to the purification and identification of the bioactive peptides obtained from the cocoa extracts. Given that the peptides present in the extract are of a different amino acid length and considering that the bioactive peptides of interest have between 5 and 20 amino acids, different purification strategies can be carried out both for removing unwanted peptides and for isolating and concentrating the peptides object of the invention. For example, fractions of a different molecular weight can be obtained from the hydrolyzed products by means of ultrafiltration, active subfractions being able to be later isolated by means of ion exchange or hydrophobic interaction concentration or high performance reverse phase or gel filtration chromatography.

The advantages of the present invention are not only due to the peptides shown in Table 4 referred to as SEQ. ID. No. 1, SEQ. ID. No. 2, SEQ. ID. No. 3, SEQ. ID. No. 4, SEQ. ID. No. 5, SEQ. ID. No. 6, SEQ. ID. No. 7, SEQ. ID. No. 8, but rather due to the raw material used from which said peptides can be obtained or initially be present, due to the whole hydrolyzed products and due to the fractions obtained from the initial cocoa having bioactive properties, simultaneously showing inhibitory activity not only of the ACE enzyme but also of the PEP enzyme, and/or antioxidant activity. Both the peptides and the extracts containing them could be incorporated in functional foods as well as be a part of pharmaceutical or dietetic compounds, and be used to help in the treatment and prevention of different diseases, especially cardiovascular disease and cerebral degeneration.

Furthermore, the bioactive peptides identified in the hydrolyzed products (Table 4) can be obtained by chemical and/or enzyme synthesis of peptides or by recombinant methods know by the person skilled in the art.

EXAMPLES

The following examples illustrate the invention though they must not be considered as limiting the scope thereof.

Example 1

Obtaining the Cocoa Extract

The Forastero variety cocoa from the Ivory Coast was used to carry out the process.

The process of obtaining the bark was performed with fresh cocoa seeds obtained from cocoa pods according to the process described in patent document ES 2 286 947 A1, of the same authors of the present invention. The product obtained after defatting by pressing is referred to as cake if it is from dehusked beans or bark if it is from beans with the husk, as in the case of the present invention.

To obtain the cocoa extract, the bark which had been defatted by pressing in a continuous mechanical extractor, and had a fat content of 10-12% was dissolved in distilled water at a 1:10 (w:v) ratio and was maintained with stirring for 1 hour at a temperature of 50° C. After dissolving in water, centrifugation at 4000 rpm for 15 minutes was performed, the supernatant was recovered and was concentrated with a rotary evaporator at 60° C. until dryness. It was left in an oven at 80° C. for 18 hours and the cocoa powder was recovered and dissolved until reaching the concentration of 0.1 mg/ml.

Said extract had the following characteristics: sugars=5.63 g/100 g; fats=10.61 g/100 g; proteins=1459 µg/ml; ACE inhibition=73.9% ($IC_{50}$=5.3 µl) and PEP inhibition=74.8% ($IC_{50}$=22.4 µl)

Example 2

Purification of the Cocoa Extract Peptides

The supernatants obtained after centrifugation of the concentrated powder were dissolved in a volume of water until reaching the concentration of 0.1 g/ml and were then filtered through a 0.45 µm membrane, thus being prepared to start the purification process by means of several chromatographic steps.

The first step of the process consisting of subjecting each of the samples to a concentration phase by means of hydrophobic interaction chromatography, in an ÄKTA Explorer chromatographic system (GE Healthcare, Amersham Biosciences AB). The HiPrep 16/10 Phenyl FF (high sub) column was used to that end and the balancing buffer (100 mM sodium phosphate, 1.5 M $(NH_4)_2SO_4$, pH=7) with a gradient of 1.5 at 0 M of $(NH_4)_2SO_4$ was used for the subsequent elution. Said elution was monitored at 214 nm and the biological activities of interest were evaluated in each of the 10 ml fractions obtained. Those having activity were subjected to a purification step by means of a first ultrafiltration, using 10 kDa filters (Amicon Ultra, Millipore), and subsequent reverse phase chromatography of the fraction less than 10 kDa, using the RESOURCE RPC 3 ml (Amersham Biosciences) column in an ÄKTA Explorer chromatographic system (Amersham Biosciences) and using a broad elution gradient with the eluents 0.1% TFA in milliQ water (A) and 0.1% TFA in acetonitrile (B). The sample was monitored at 214 nm and the relevant biological activities were again evaluated in each of the fractions obtained, in this case the 2 ml fraction, after removing the solvents used in the process, in this case, the ACE and PEP enzyme inhibition assays were performed in vitro.

Example 3

Obtaining the Cocoa Extract Rich in Bioactive Peptides

According to what has been described in Example 1, the cocoa extract was treated for one hour at 50° C. with a combination of the enzymes Termamyl and Alcalase, at a concentration of 1 µl/g of each of them. After one hour, the enzymes were deactivated, centrifugation lasting about 15 minutes at 4000 rpm was performed, and the supernatant rich in peptides was collected and the ACE and PEP inhibition assay was carried out.

A. —Measurement of the ACE Inhibitory Activity

The ACE activity was measured according to the method described by Cushman and Cheung (Cushman D W, Cheung H S. 1971. Biochem Pharmacol 20:1637-1648) later modified by Nakamura (Nakamura Y, Yamamoto N, Sakai K et al. 1995. J Dairy Sci 78:777-783). This method is based on using Hippuryl-L-Histidyl-L-Leucine (Hip-His-Leu) as a substrate, because the action of ACE on said substrate produces the release of hippuric acid, which can be spectrophotometrically quantified by reading the absorbance at 228 nm after extraction with ethyl acetate.

The Hip-His-Leu was dissolved in 0.1 M sodium borate buffer (pH 8.3) which contained 0.3 M of NaCl. Then 200 µl of the solution of Hip-His-Leu were added and it was mixed with 80 µl of the ACE inhibitory peptide solution. The pH was adjusted to 8.3 and the mixture was incubated for 3 minutes at 37° C. The reaction was initiated by adding 20 µl of ACE dissolved in distilled water (0.1 U/ml) and the mixture was incubated for 30 minutes a 37° C. The reaction was detained by adding 250 µl of 1 N HCl. The hippuric acid released by the ACE was extracted with ethyl acetate, which was removed by vacuum evaporation, the residue being dissolved in 1 ml of distilled water, and the optical density of the sample was measured at 228 nm.

The inhibition was measured and expressed as a percentage and also as the concentration of the components inhibiting 50% of the ACE activity ($IC_{50}$). The result was 67.8%.

Once the ACE inhibition in vitro of the hydrolyzed extract was determined, it was fractionated and the ACE inhibition of the fractions obtained by hydrophobic interaction chromatography was measured. FIG. 1 shows the hydrophobic interaction chromatograph of the hydrolyzed bark extract.

The ACE inhibition of all the collected fractions was measured and the inhibition results are shown in Table 1.

TABLE 1

Percentage of ACE inhibition by the hydrophobic interaction fractions.

| Hydrophobic interaction | % ACE inhibition |
| --- | --- |
| F1 | 18.575 |
| F2 | 28.499 |
| F3 | 0 |
| F4 | 34.606 |
| F5 | 40.967 |
| F6 | 0 |
| F7 | 10.941 |
| F8 | 4.834 |
| F9 | 0 |
| F10 | 0 |
| F11 | 0 |

The fractions with greater ACE inhibitory activity were F4 and F5 and reverse phase purification of these two fractions separately was achieved.

Figure 2:
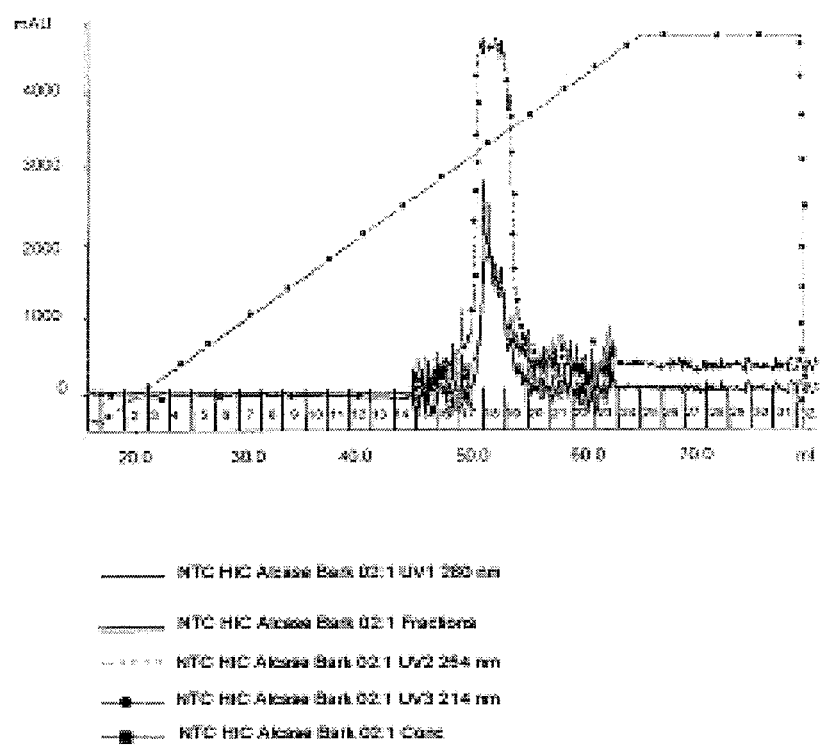
FIG. 2 shows a reverse phase chromatograph of the hydrophobic interaction F4.
Figure 3:
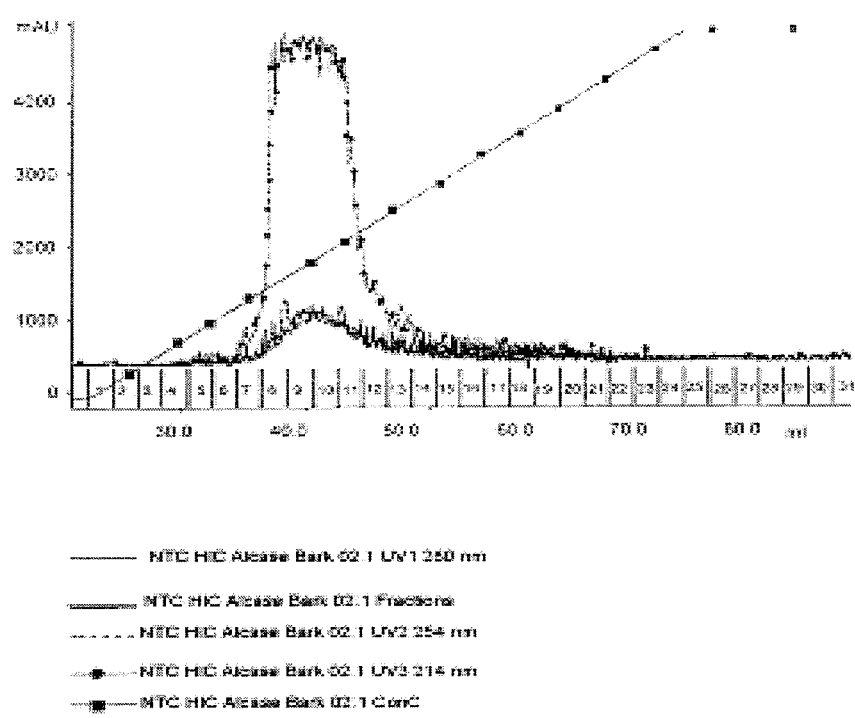
FIG. 3 shows a reverse phase chromatograph of the hydrophobic interaction F5.

FIGS. 2 and 3 contain the reverse phase chromatographs of hydrophobic interaction fractions 4 and 5, respectively.

The ACE inhibition of fractions 15, 16, 17, 18, 19, 20, 21, 22 and 23 from hydrophobic interaction fraction 4 and fractions 7, 8, 9, 10, 11, 12, 13, 14 and 15 from the hydrophobic interaction fraction 5 was measured. The inhibition results are shown in Tables 2 and 3, respectively.

TABLE 2

Percentage of ACE inhibition by the reverse phase fractions from hydrophobic interaction fraction 4.

| Reverse phase (F5HIC) | % ACE inhibition |
|---|---|
| F7 | 0 |
| F8 | 16.795 |
| F9 | 0 |
| F10 | 0 |
| F11 | 25.621 |
| F12 | 16.281 |
| F13 | 11.911 |
| F14 | 12.768 |
| F15 | 4.37 |

TABLE 3

Percentage of ACE inhibition by the reverse phase fractions from hydrophobic interaction fraction 5.

| Reverse phase (F5HIC) | % ACE inhibition |
|---|---|
| F7 | 0 |
| F8 | 16.795 |
| F9 | 0 |
| F10 | 0 |
| F11 | 25.621 |
| F12 | 16.281 |
| F13 | 11.911 |
| F14 | 12.768 |
| F15 | 4.37 |

The four reverse phase fractions with the highest inhibition in vitro of the ACE enzyme (F18HIC4, F11HICF5, F12HICF5, F14HICF5) were analyzed by MALDI-TOF and the peptides present therein responsible for said inhibition were identified.

Table 4 contains the peptide sequences identified by MS/MS ACE inhibitors.

TABLE 4

Peptide sequences identified by MS/MS ACE inhibitors.

| Observed molecular mass (Da) | PEPTIDE SEQUENCE | PROTEIN |
|---|---|---|
| 1201.431 | SDNEWAWMF | SEQ. ID. No. 1 |
| 1298.55 | LSDNEWAWMF | SEQ. ID. No. 2 |
| 1313.5292 | SDNEWAWMFK | SEQ. ID. No. 3 |
| 1442.608 | LSDNEWAWMFK | SEQ. ID. No. 4 |
| 1489.7651 | RRSDLDNGTPVIF | SEQ. ID. No. 5 |
| 1555.68 | DNYDNSAGKWWVT | SEQ. ID. No. 6 |
| 1641.7644 | TSTVWRLDNYDNSA | SEQ. ID. No. 7 |
| 1771.7483 | DNYDNSAGKWWVTTD | SEQ. ID. No. 8 |

B. —Measurement of the PEP Inhibitory Activity.

The prolyl endopeptidase activity was measured following the method described by Yoshimoto (Yoshimoto, T. and Tsuru, D. 1978. Agr. Biol. Chem., 42, 2417; Yoshimoto, T., Walter, R. and Tsuru, D. 1980. J. Biol. Chem., 255, 4786), which is based on using the substrate Z-Gly-Pro-p-nitroaniline, from which p-nitroaniline is released by the action of the PEP enzyme, which can be spectrophotometrically quantified by reading the absorbance at 410 nm.

The PEP inhibitory activity was determined by adding the sample to be assayed to the reaction mixture, in this case the PEP inhibitory activity was measured with the same hydrolyzed extract obtained from the bark and proteolytic enzymes previously used for the ACE determination.

The inhibition was measured and expressed as a percentage and also as the concentration of the components inhibiting 50% of the PEP activity ($IC_{50}$). The result was 74.8% ($IC_{50}$=0.0946 mg).

Once the PEP inhibition in vitro of the hydrolyzed bark extract was determined, the PEP inhibition of all the purification fractions obtained by reverse phase from hydrophobic interaction fractions 4 and 5 was tested, as was done with the ACE enzyme.

Tables 5 and 6 contain the PEP enzyme inhibition values of the chromatographic fractions obtained in the reverse phase purification from hydrophobic interaction fractions 4 and 5, respectively.

TABLE 5

Percentage of PEP inhibition by the reverse phase fractions from hydrophobic interaction fraction 4.

| Reverse phase (F4HIC) | % PEP inhibition |
|---|---|
| F15 | 19.7309417 |
| F16 | 21.07623318 |
| F17 | 9.417040359 |
| F18 | 38.11659193 |
| F19 | 33.632287 |
| F20 | 21.52466368 |
| F21 | 21.07623318 |
| F22 | 29.9058296 |
| F23 | 22.86995516 |

TABLE 6

Percentage of PEP inhibition by the reverse phase fractions from hydrophobic interaction fraction 5.

| Reverse phase (F5HIC) | % PEP inhibition |
|---|---|
| F8 | 22.42152466 |
| F9 | 32.28699552 |
| F10 | 25.56053812 |
| F11 | 63.22869955 |
| F12 | 43.49775785 |
| F13 | 30.94170404 |
| F14 | 21.07623318 |
| F15 | 8.520179372 |

These results allow concluding that the four fractions with the highest ACE inhibition in which different peptides responsible for this inhibition have been identified are the fractions with the highest inhibition of the PEP enzyme.

It should therefore be pointed out that the peptides identified after hydrophobic interaction and reverse phase purification of a bark extract treated with proteases are responsible for the inhibition both of the ACE enzyme and of the PEP enzyme.

Example 4

Evaluation of the Antioxidant Capacity of the Extracts in *C. elegans*

A. Selection of Fractions with High Enzyme Inhibition

The purpose of this study consisted of evaluating in vivo the functionality of the extracts which gave a positive result in the inhibition of prolyl endopeptidase in vitro. To that end, the Caenorhabditis elegans model organism was used. Said functionality is related to the protection that said extracts can confer in the development of neurodegenerative Alzheimer's disease.

The four fractions that gave positive results in the inhibition of prolyl endopeptidase in vitro and the peptides of which present therein have been identified have been selected. They are reverse phase fraction 18 from hydrophobic interaction fraction 4 (F18HIC4) and reverse phase fractions 11, 12 and 14 from hydrophobic interaction fraction 5 (F11HICF5, F12HICF5, F14HICF5).

B. Assay of the Fractions with High Inhibitory Activity in C. elegans In Vivo

An oxidative stress assay using the CL4176 transgenic strain of C. elegans was carried out, characterized by expressing the human amyloid beta-peptide (Abl-42) after temperature induction.

Prior data in the literature indicate that the formation of amyloid beta-peptide plaques is preceded by oxidative stress (Drake et al, "Oxidative stress precedes fibrillar deposition of Alzheimer's disease amyloid beta-peptide (1-42) in a transgenic Caenorhabditis elegans model" Neurobiol Aging 2003, 24(3):415-20). Therefore, it is interesting to evaluate if the hypothetical reduction of fibrillar deposition of Ab peptides in the neurons produced by the action of a molecule or compound gives rise to greater resistance against oxidative stress treatments. Furthermore, the expression of said peptide in these transgenic animals produces a paralysis that can be evaluated after adding the molecule or compound of interest.

To carry out the experiment, worms of the CL4176 strain having a synchronized age by means of plate cultivation of NG at 16° C. were obtained. The eggs were collected in NG plates which contained 100 µl of each peptide fraction (F11, F12, F14 and F18). Z-prolyl prolinal (100 µl of a 10 mM stock on the plate surface) was used as a positive control. The final concentration was 0.1 mM. NG medium was used as a negative control. After 2 days of incubation, the temperature was increased to 23° C. to induce the expression of Ab peptide. For the first 3 days after induction, the number of worms paralyzed in each assayed condition was analyzed. After 7 days of incubation in said conditions, the worms were subjected to oxidative stress. To that end, those which did not present signs of paralysis were transferred to plates with S medium with $H_2O_2$ (2 mM). The plates were incubated at 23° C. and after 5 hours the total number of worms that survived treatment were counted.

Figure 4:
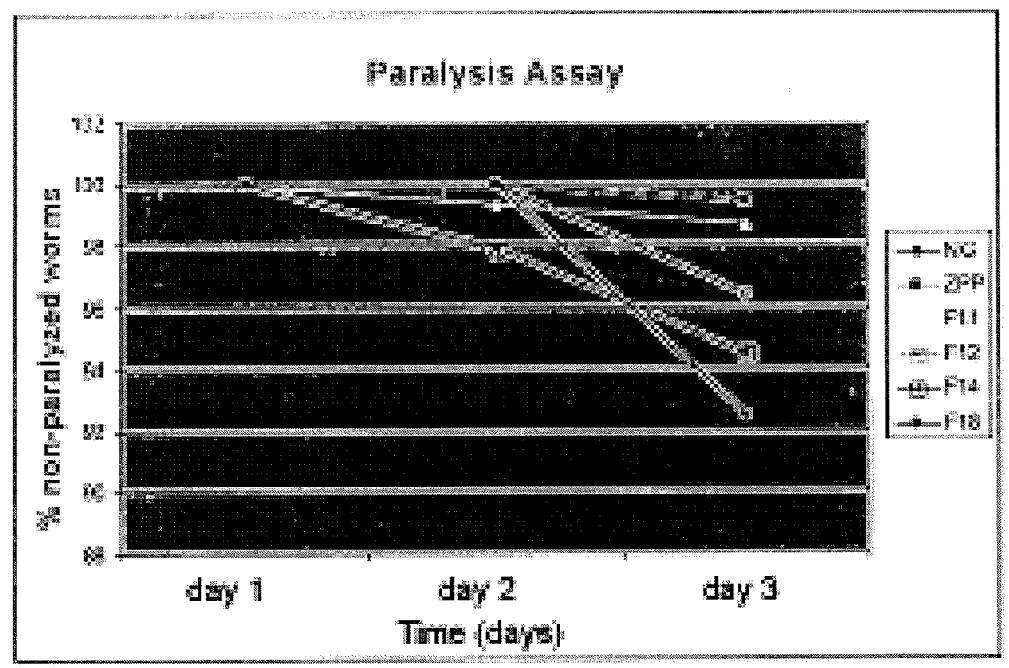
FIG. 4 shows the percentage of non-paralyzed worms observed in each of the assayed conditions after inducing the expression of Ab peptide.

C. Results of the Paralysis and Oxidative Stress Assay of the Caenorhabditis elegans Model Organism with the Identified Peptide Fractions FIG. 4 shows the percentage of non-paralyzed worms for the first 3 days after inducing the expression of Ab peptide. In control conditions (NG), the percentage of non-paralyzed worms is reduced to 96.4% on the third day, while with the positive control (Z-prolyl prolinal) the percentage of non-paralyzed worms is maintained at 99.44%.

Of the four fractions used, fraction 11 showed the greatest paralysis-reducing effect. In this case, it was determined that 98.64% remained without paralysis on the third day of incubation. The F12, F14 and F18 fractions gave rise to a lower reduction of the paralysis, being observed at 96.4, 94.48, and 92.46% of non-paralyzed worms respectively on the third day.

Figure 5:
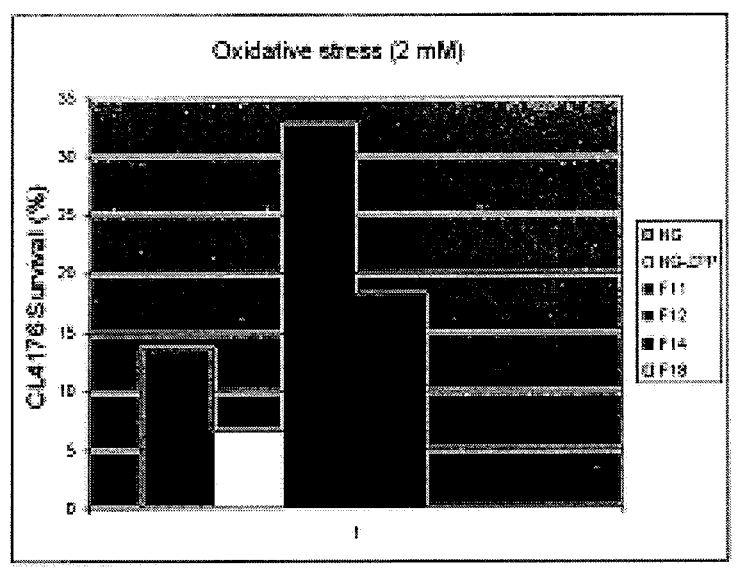
FIG. 5 shows the survival of the CL4176 strain obtained after applying stress with $H_2O_2$ (2 mM) and after 1 week of incubation with the different extracts (F11, F12, F14, F18). ZPP: Z-prolyl prolinal.

FIG. 5 shows the percentage of worm survival after 5 hours of applying oxidative stress with $H_2O_2$ (2 mM). In the case of the worms that had been cultivated in NG with the F11 fraction, the highest survival percentage (32.6%) could be determined, being higher than that reached in NG control conditions (13.7%). The F12 fraction also provided greater protection against oxidative stress, obtaining a survival of the 18.2%. Finally, survival was not observed in the case of worms cultivated in the presence of the F14 and F18 fractions.

These results allow concluding that the CL4176 worms cultivated in the presence of the F11 fraction present a progressive reduction of paralysis produced by the accumulation of amyloid peptide (Ab) in neuronal cells. These worms have shown greater resistance to the oxidative stress treatment that is possibly produced, in part, by the four peptides of the eight identified, present in that fraction the sequences of which are RRSDLDNGTPVIF (SEQ ID NO: 5), DNYDNSAGKWWVT (SEQ ID NO: 6), TSTVWRLDNYDNSA (SEQ ID NO: 7), DNYDNSAGKWWVTTD (SEQ ID NO: 8). It should be pointed out that fraction 12 also produces this effect, though to a lesser degree, and three peptides having sequences SDNEWAWMFK (SEQ ID NO: 3), LSD-NEWAWMFK (SEQ ID NO: 4)+oxidation and SDNEWAWMF (SEQ ID NO: 1)+oxidation were identified therein.

The invention claimed is:

1. A composition comprising a non-naturally occurring carrier and a bioactive product obtained by enzymatic hydrolysis from cocoa extracts, consisting of the peptide represented by SEQ. ID. No. 6 having PEP inhibitory activity, antidegenerative and/or antioxidant activity.

2. The composition according to claim 1, characterized in that the bioactive product obtained by enzymatic hydrolysis from cocoa extracts is obtained from a cocoa product with husk referred to as bark.

3. The composition according to claim 2, characterized in that the bark has been defatted by means of physical pressing, until having between 5% and 15% fat.

4. The composition according to claim 3, characterized in that the defatted product is dissolved in water (5% to 20%) and is subjected to a step of enzymatic hydrolysis, adding one or more enzymes to the aqueous solution obtained and maintaining the temperature between 40° C. and 60° C., for a time period of 1 to 24 hours, at a suitable pH.

5. The composition according to claim 1, characterized in that the enzymatic hydrolysis is carried out with one or more enzymes from the group of Termamyl, Alcalase, Neutrase, Ultraflo or Flavourzyme.

6. The composition according to claim 1, characterized in that the bioactive peptide is obtained by centrifugation from the supernatant of the hydrolyzed extract once hydrolysis has ended.

7. The composition according to claim 1, characterized in that once the supernatant of the hydrolyzed extract is concentrated, it has ACE inhibitory activity in vitro of 73.9% ($IC_{50}$=0.4039 mg).

8. The composition according to claim 1, characterized in that once the supernatant of the hydrolyzed extract is concentrated, it has a PEP inhibitory activity in vitro of 74.8% ($IC_{50}$=0.0946 mg).

9. A method of preparing a functional food comprising adding a non-naturally occurring carrier and a bioactive product consisting of the peptide of SEQ. ID. No. 6, as a food ingredient in an effective amount to produce the functional food having antidegenerative and/or antioxidant activity.

* * * * *

SEQUENCE LISTING

```
<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 1

Ser Asp Asn Glu Trp Ala Trp Met Phe
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic oligopeptide

<400> SEQUENCE: 2
```

```
Leu Ser Asp Asn Glu Trp Ala Trp Met Phe
1               5                   10
```

<210> SEQ ID NO 3
<211> LENGTH: 10
<212> TYPE: PRT
<213> ORGANISM: Artificial Sequence
<220> FEATURE:
<223> OTHER INFORMATION: Synthetic oligopeptide

<400> SEQUENCE: 3

```
Ser Asp Asn Glu Trp Ala Trp Met Phe Lys
1               5                   10
```

<210> SEQ ID NO 4
<211> LENGTH: 11
<212> TYPE: PRT
<213> ORGANISM: Artificial Sequence
<220> FEATURE:
<223> OTHER INFORMATION: Synthetic oligopeptide

<400> SEQUENCE: 4

```
Leu Ser Asp Asn Glu Trp Ala Trp Met Phe Lys
1               5                   10
```

<210> SEQ ID NO 5
<211> LENGTH: 13
<212> TYPE: PRT
<213> ORGANISM: Artificial Sequence
<220> FEATURE:
<223> OTHER INFORMATION: Synthetic oligopeptide

<400> SEQUENCE: 5

```
Arg Arg Ser Asp Leu Asp Asn Gly Thr Pro Val Ile Phe
1               5                   10
```

<210> SEQ ID NO 6
<211> LENGTH: 13
<212> TYPE: PRT
<213> ORGANISM: Artificial Sequence
<220> FEATURE:
<223> OTHER INFORMATION: Synthetic oligopeptide

<400> SEQUENCE: 6

```
Asp Asn Tyr Asp Asn Ser Ala Gly Lys Trp Trp Val Thr
1               5                   10
```

<210> SEQ ID NO 7
<211> LENGTH: 14
<212> TYPE: PRT
<213> ORGANISM: Artificial Sequence
<220> FEATURE:
<223> OTHER INFORMATION: Synthetic oligopeptide

<400> SEQUENCE: 7

```
Thr Ser Thr Val Trp Arg Leu Asp Asn Tyr Asp Asn Ser Ala
1               5                   10
```

<210> SEQ ID NO 8
<211> LENGTH: 15
<212> TYPE: PRT
<213> ORGANISM: Artificial Sequence -continued

```
<220> FEATURE:
<223> OTHER INFORMATION: Synthetic oligopeptide

<400> SEQUENCE: 8

Asp Asn Tyr Asp Asn Ser Ala Gly Lys Trp Trp Val Thr Thr Asp
1               5                   10                  15
```